US00PP11084P

United States Patent [19]

Plate

[11] Patent Number: Plant 11,084

[45] Date of Patent: Oct. 12, 1999

[54] SINNINGIA PLANT NAMED 'GLO WHITE'

[75] Inventor: Renate Plate, Bremen, Germany

[73] Assignee: Wolfgang Bock Pflanzenexport KG, Bremen, Germany

[21] Appl. No.: 08/933,400

[22] Filed: Sep. 19, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Kent L. Bell
*Attorney, Agent, or Firm*—Foley & Lardner

[57] ABSTRACT

A new and distinct variety of Sinningia×hybrida plant named 'Glo White', particularly characterized by its large pure white, velvet textured double flowers clustered in the center of the plant. The plants grow very quickly, becoming marketable in approximately 12 weeks, and are very floriferous, often having 4–6 flowers open at a given time.

1 Drawing Sheet

The present invention comprises a new and distinct cultivar of Sinningia×hybrida, a genus in the family Gesneriaceae, and referred to by the cultivar name 'Glo White'. The new cultivar is a hybrid selected from the progeny of a cross of parent plants identified below.

Hybrids of *Sinningia speciosa*, or Gloxinia as they are commonly known, are popular potted plants which may be cultivated indoors or in greenhouses. They are distinguished by their large, showy velvet textured flowers which come in various shades of violet, rose, red, or white.

Sinningia are typically propagated from seeds, or by leaf cuttings or tissue culture. The new cultivar is a sterile hybrid which does not produce any seeds and is asexually propagated by tissue culture.

The new cultivar is a product of a breeding program carried out by the inventor Renate Plate in Bremen, Germany. The new cultivar 'Glo White' is a result of several generations of crosses of selected, but unnamed *Sinningia speciosa* made by the inventor in Germany beginning in 1994. The new cultivar 'Glo White' was discovered from the progeny of the stated cross by Renate Plate in 1995. Asexual propagation by tissue culture done under the supervision of the inventor in laboratories in Bremen, Germany was used to increase the number of plants for evaluation and has demonstrated the stability of the combination of the plant from generation to generation.

The following observations, measurements and values describe plants grown in Apopka, Fla. in greenhouse conditions which are typical of those generally used in horticultural practice.

The following traits have been repeatedly observed to be characteristics which in combination distinguish 'Glo White' from generally available seedling-derived Sinningia common in commercial cultivation:

1. The flowers produced by 'Glo White' are double, large, pure white in color, and are clustered in the center of the plant.

2. Plants of 'Glo White' have a short, compact growth habit, and are suitable for cultivation in 10–12 cm pots.

3. Plants of 'Glo White' are very floriferous, typically having 4–6 or more flowers open at a given time, and 12 or more buds in various stages of development and which open in successon. Once in bloom, the plant typically remains in bloom for 12 weeks.

4. Plants of 'Glo White' grow very quickly, producing marketable flowering plants in approximately 12 weeks.

It is difficult to compare the new cultivar with seed-derived Sinningia which are heterogeneous genetically, and therefore lack uniformity in flower color and quality. By comparison, 'Glo White' is a single superior genotype asexually propagated preferably by tissue culture. Thus, its combined horticultural properties listed above are uniform and predictable.

All color references are measured against The Royal Horticultural Society color chart. Colors are approximate as color depends on horticultural practices such as light level and fertilization rate, among others, without, however, any change in genotype.

The color photographic drawing comprises a top perspective view of the flowers and foliage of a plant of 'Glo White' grown in a 15 cm pot. The photograph was taken approximately 16 weeks after planting a small cutting obtained by tissue culture and grown under appropriate growing conditions.

Colors are as accurate as possible with color illustrations of this type.

Origin: Seedling from a cross of selected, but named *Sinningia speciosa* hybrids.

Classification: Sinningia×hybrida, cv 'Glo White'.

Propagation: Asexual propagation by tissue culture or leaf cuttings.

FLOWERS

Calyx: 6–8 lobed, lobes lanceolate, acutely tapered. Approximately 2.5 cm to 2.8 cm long, and 1.0 cm to 1.3 cm wide. Adaxial color is greener than, but closest to 146 A–B; abaxial color is 146 B.

Corolla: Campanulate, outermost whorl has approximately 6 lobes. Secondary inner whorls of corolla are ruffled in appearance. The number of lobes is variable, 8 to 10. Corolla approximately 6.2 cm to 7.0 cm long, and 7.8 cm to 9.0 cm in diameter. The adaxial color when flower is fully open is pure white 155 D throughout. The abaxial color is 155 D, with occasional streaks of 144 A on the outermost whorl. The corolla darkens to 165 C with senescence.

Peduncle: Approximately 9.0 cm to 11.1 cm long, and 5 mm to 6 mm in diameter measured at the midpoint between the calyx and the stem. Color is 146 D.

Bud: Tightly folded, enclosed in the calyx, round, 0.8–1.5 cm in width, light green in color, R.H.S. 147 C–D, but it rapidly expands and partially opens/unfolds to take on the colors of the mature flower.

Flowering habit: Flowers borne singularly, carried above the foliage, one flower per stem, frequently with two to three flower stems per leaf node.

Arrangement of flowers: The flowers are clustered together above the foliage in the center of the plant. Once in full bloom, the flowers appear to be spread over the entire plant.

Texture of flowers: Thick and velvety in appearance.

Quantity of bloom: Plants of 'Glo White' are very floriferous, typically having 4–6 or more flowers open at a given time, and 12 or more buds in various stages of development and which open in succession.

Duration of bloom: Once in bloom, the plant typically remains in bloom for approxiamately 12 weeks. Individual flowers remain open for approximately 14 days before senescing.

Fragrance: None.

Reproductive organs: Stamens and anthers are frequently reduced and petaloid. Stamens are approximately 2.2 cm long and 1.0 mm wide, and 155 D in color. Anthers are approximately 3 mm long and 2 mm wide, and 199 A in color. Pollen is 159 B in color. Style and stigma are misshapen and frequently petaloid, 155 D in color, and approximately 2.2 cm long and 3.0 mm in diameter; ovary is reduced in size.

Seed characteristics: Sterile hybrid.

PLANT

Form: Basal rosettes of rugose velvet texture, elliptic, paired, opposite leaves arranged around short stems.

Height: Approximately 18 cm to 22 cm, including flowers.

Diameter: Approximately 36 cm to 40 cm.

Stems: Approximately 0.7 cm to 1.2 cm diameter; internodes approximately 0.6 cm to 1.4 cm. Stem color is 146 C D.

Resistance to pests and disease: Typical, no special observations made.

FOLIAGE

Size of leaf: The largest leaves are approximately 15 cm to 16.5 cm long, and 13.5 cm to 14.7 cm wide. Average sized leaves are approximately 13.5 cm to 14.4 cm long, and 9 cm to 10 cm wide.

Shape of leaf: The leaf blade is ovate with an obtuse to cordate base and an obtuse to acute tip. The leaf petioles are approximately 4.3 cm to 6.0 cm long and 0.7 cm in diameter measured at the midpoint between the stem and the leaf. The leaf margins are crenate, and somewhat wavy. The leaf blade may be flat or cupped.

Surface texture: The upper surfaces of the leaf are rugose and pubescent. The veins and midrib are sunken on the upper surface, and protruding on the lower surface. The color of the veins and midrib is 146 D on the adaxial surface and 148 C on the abaxial surface.

Color: The leaves are dark green throughout. The adaxial surface is 139 A. The abaxial surface is 148 C. The petioles are 146 D.

ROOTS

Stems arise from a fleshy tuber which is approximately 2.0 cm to 2.2 cm in diameter at the time of flowering. The tuber is brownish white, and has numerous greenish white to brown fibrous roots.

I claim:

1. A new and distinct cultivar of Sinningia×hybrida plant named 'Glo White', as illustrated and described.

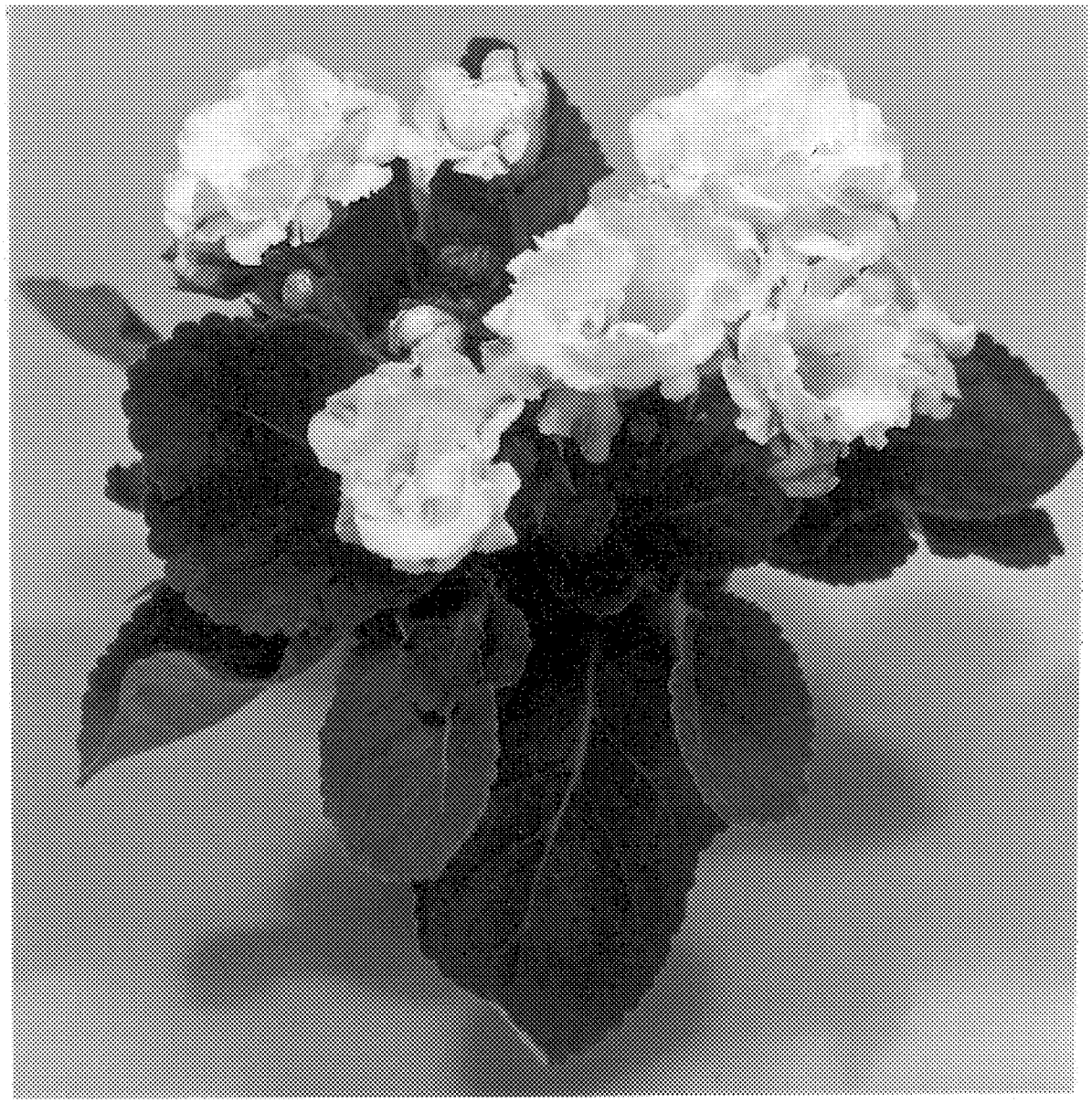

* * * * *